(12) United States Patent
Kim et al.

(10) Patent No.: US 11,081,728 B2
(45) Date of Patent: Aug. 3, 2021

(54) NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME

(71) Applicant: LG Chem, Ltd., Seoul (KR)

(72) Inventors: Hyun Seung Kim, Daejeon (KR); Sung Hoon Yu, Daejeon (KR)

(73) Assignee: LG Chem, Ltd.

( * ) Notice: Subject to any disclaimer, the term of this patent is extended or adjusted under 35 U.S.C. 154(b) by 219 days.

(21) Appl. No.: 16/338,578

(22) PCT Filed: Jul. 6, 2018

(86) PCT No.: PCT/KR2018/007730
§ 371 (c)(1),
(2) Date: Apr. 1, 2019

(87) PCT Pub. No.: WO2019/013502
PCT Pub. Date: Jan. 17, 2019

(65) Prior Publication Data
US 2020/0044286 A1 Feb. 6, 2020

(30) Foreign Application Priority Data

Jul. 14, 2017 (KR) .................. 10-2017-0089774
Jul. 4, 2018 (KR) .................. 10-2018-0077559

(51) Int. Cl.
*H01M 10/0567* (2010.01)
*C07D 341/00* (2006.01)
(Continued)

(52) U.S. Cl.
CPC ...... *H01M 10/0567* (2013.01); *C07D 341/00* (2013.01); *H01M 4/505* (2013.01);
(Continued)

(58) Field of Classification Search
None
See application file for complete search history.

(56) References Cited

U.S. PATENT DOCUMENTS

| 2007/0187650 | A1 | 8/2007 | Anders et al. |
| 2012/0171531 | A1 | 7/2012 | Park et al. |

(Continued)

FOREIGN PATENT DOCUMENTS

| JP | 2001185215 A | 7/2001 |
| JP | 2010117635 A | 5/2010 |

(Continued)

OTHER PUBLICATIONS

Andrzej Bobrowski et al: "Complexation of macrocyclic ligands with relatively non-solvated metal ions generated in dichloromethane by electrochemical oxidation of amalgam electrodes", Inorganica Chimica Acta, vol. 293, No. 2, Oct. 15, 1999, p. 223-228, XP055626251.

(Continued)

*Primary Examiner* — Wyatt P McConnell
(74) *Attorney, Agent, or Firm* — Lerner, David, Littenberg, Krumholz & Mentlik, LLP (57) ABSTRACT

The present invention relates to a non-aqueous electrolyte solution additive, and a non-aqueous electrolyte solution for a lithium secondary battery and a lithium secondary battery which include the same, and particularly, to a non-aqueous electrolyte solution additive including a compound based on a cyclic sulfur structure, and a secondary battery in which low-voltage failure due to metal dissolution may be improved by including the same.

15 Claims, 2 Drawing Sheets

(51) Int. Cl.
| | |
|---|---|
| *H01M 4/505* | (2010.01) |
| *H01M 4/525* | (2010.01) |
| *H01M 10/0525* | (2010.01) |
| *H01M 10/0568* | (2010.01) |
| *H01M 10/0569* | (2010.01) |
| *H01M 4/02* | (2006.01) |

(52) U.S. Cl.
 CPC ....... *H01M 4/525* (2013.01); *H01M 10/0525* (2013.01); *H01M 10/0568* (2013.01); *H01M 10/0569* (2013.01); *H01M 2004/028* (2013.01); *H01M 2300/0025* (2013.01)

(56) References Cited

U.S. PATENT DOCUMENTS

| | | |
|---|---|---|
| 2014/0377666 A1 | 12/2014 | Kodama et al. |
| 2017/0125847 A1 | 5/2017 | Yu et al. |
| 2018/0166749 A1 | 6/2018 | Ono et al. |

FOREIGN PATENT DOCUMENTS

| | | |
|---|---|---|
| JP | 2011060464 A | 3/2011 |
| JP | 2013149429 A | 8/2013 |
| JP | 2015118782 A | 6/2015 |
| KR | 20120078391 A | 7/2012 |
| KR | 101335467 B1 | 11/2013 |
| KR | 20140133568 A | 11/2014 |
| KR | 20160076192 A | 6/2016 |
| KR | 20170052493 A | 5/2017 |
| WO | 9962898 A2 | 12/1999 |
| WO | 2013151096 A1 | 10/2013 |
| WO | 2016194995 A1 | 12/2016 |

OTHER PUBLICATIONS

Colton R et al: "Interactions of some crown ethers, cyclam and its tetrathia analogue with alkali, alkali earth and other metal ions: an electrospray mass spectrometric study", Inorganica Chimica Acta, Elsevier BV, NL, vol. 231, No. 1-2, Mar. 15, 1995, p. 87-93, XP004818441.
Extended European Search Report including Written Opinion for Application No. EP18832899.1 dated Oct. 8, 2019.
Hojo M et al: "Polarographic studies on the interaction between macrocyclic compounds and cations or acids in acetonitrile", Journal of Electroanalytical Chemistry and Interfacial Electrochemistry, Elsevier, Amsterdam, NL, vol. 234, No. 1-2, Sep. 28, 1987, p. 251-261, XP026517692.
Toshio Takido et al: "A Novel Synthesis of Cyclic Polythioethers Using Liquid-Liquid Phase-Transfer Catalysis", Phosphorus, Sulfur and Silicon and the related elements, Taylor & Francis Inc, US, vol. 178, No. 6, Mar. 1, 2003, p. 1295-1301, XP009174515.
Antonella Dalla Cort et al., Macrocyclization under Kinetic Control. A Theoretical Study and Its Application to the Synthesis of Macrocyclic Poly( thiolactones), Journal of the American Chemical Society, Aug. 1994, 116, pp. 7081-7087.
Hajime Katano et al., Voltammetric Study of the Facilitated Transfer of Lead(II) Ion by Macrocyclic Polythiaether 1,4,7,10,13,16-Hexathiacyclooctadecane across the Polarizable Nitrobebzene/Water Interface, Analytical Sciences, Nov. 29, 1996, vol. 12, No. 5, pp. 683-689.
Hyun-seung Kim et al., An azamacrocyclic electrolyte additive to suppress metal deposition in lithium-ion batteries, Electrochemistry Communications, 58 (Sep. 2015), pp. 25-28.
Shinichi Komaba et al., Influence of manganese(II), cobalt(II), and nickel(II) additives in electrolyte on performance of graphite anode for lithium-ion batteries, Electrochimica Acta, 47 (Feb. 1, 2002), pp. 1229-1239.
C. Robert Lucas et al., Macrocyclic thioether-esters and thioether-thioesters and their palladium, platinum and silver complexes, Inorganica Chimica Acta 230 (Mar. 1, 1995) pp. 133-138.
Tomoo Sarukawa et al., Electrochemical Activity of Sulfur-Linked Tetrathionaphthalene Polymer, Journal of the Electrochemical Society, Feb. 1, 2010, vol. 157, No. 2, pp. F23-F29.
K. S. Siddiqi et al., Synthesis and Reactivity in Inorganic and Metal-Organic Chemistry, Synthesis and Reactivity in Inorganic and Metal-Organic Chemistry,Sep. 1, 1994; 24:8, pp. 1325-1338.
International Search Report for PCT/KR2018/007730 dated Oct. 8, 2018.

NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

The present application is a national phase entry under 35 U.S.C. § 371 of International Application No. PCT/KR2018/007730 filed Jul. 6, 2018, which claims priority from Korean Patent Application No. 10-2018-0077559 filed Jul. 4, 2018 and Korean Patent Application No. 10-2017-0089774 filed Jul. 14, 2017, all of which are incorporated herein by reference.

TECHNICAL FIELD

The present invention relates to a non-aqueous electrolyte solution additive, and a non-aqueous electrolyte solution for a lithium secondary battery and a lithium secondary battery which include the same.

BACKGROUND ART

Dependence on electrical energy is gradually increasing in modern society, and, accordingly, production of the electrical energy has been further increased. In order to address environmental issues that arise during this process, renewable energy generation is in the spotlight as a next-generation power generation system. With respect to renewable energy, since it exhibits intermittent power generation characteristics, a large-capacity power storage device is indispensable to supply power stably. A lithium-ion battery, i.e., a secondary battery system, is in the spotlight as a device exhibiting the highest energy density which is currently commercialized among power storage devices.

The lithium-ion battery is the most suitable technique for various applications, wherein, since miniaturization is possible, it may be applied to personal IT devices, and it may also be applied to large devices such as power storage devices.

With respect to the lithium-ion battery, unlike the early days when lithium metal was directly used in the system, it is composed of a positive electrode formed of a transition metal oxide containing lithium, a negative electrode capable of storing the lithium, an electrolyte solution, and a separator.

With respect to the positive electrode among these components, energy is stored through a redox reaction of transition metal, wherein this results in the fact that the transition metal must be essentially included in a positive electrode material.

There is a limitation in that a specific positive electrode structure collapses during repeated charge and discharge to dissolve the transition metal in the electrolyte solution. Also, since operating potential of the positive electrode is high, the transition metal may be dissolved due to an acid generated by a side reaction with the electrolyte solution or an acid formed by hydrolysis/pyrolysis of a lithium salt.

With respect to the dissolved transition metal, although its amount is not substantially enough to contribute to the degradation of capacity of the positive electrode, it is known that even a small amount causes severe degradation of the negative electrode. That is, transition metal ions thus dissolved are electrodeposited on the negative electrode to self-discharge the negative electrode and destruct a solid electrolyte interphase (SEI) that gives passivation ability to the negative electrode, and, thus, it is known as a factor to increase interfacial resistance of the negative electrode while promoting an additional electrolyte solution decomposition reaction.

Since this series of reactions reduces an amount of available lithium ions in the battery, it becomes a major cause of the degradation of capacity of the battery. In addition, in a case in which the metal ions electrodeposited on the negative electrode grow as dendrites, since it causes an internal short-circuit of the battery, this leads to a decrease in safety of the battery.

The metal dissolution may also occur when metallic impurities are included during the preparation of an initial electrode slurry. For example, in the lithium-ion battery, the electrode is prepared by coating a slurry including a conductive agent and a binder as well as an electrode active material on a current collector, wherein, in this case, metallic foreign matter, such as iron, copper, or nickel, generated during the preparation of the conductive agent may be contained during the preparation of the electrode. There are many cases where a large amount of the metallic foreign matter exists locally in the electrode, and, as a result, during an initial charging process of the battery, an excessive amount of metal is dissolved from the positive electrode and electrodeposited on the negative electrode to grow as dendrites. As a result, this causes the internal short-circuit of the battery or becomes a cause of low-voltage failure, and thus, it is disadvantageous in that productivity is reduced.

Thus, in order to improve performance and low-voltage failure of a full cell, it is important to remove transition metal species dissolved from the positive electrode in the electrolyte solution or suppress the dissolution of the transition metal species included in the positive electrode to be electrodeposited on the surface of the negative electrode.

PRIOR ART DOCUMENT

Electrochem. Acta, 47 (2002), 1229-1239
Electrochem. Commun. 58 (2015) 25-28

DISCLOSURE OF THE INVENTION

Technical Problem

An aspect of the present invention provides a non-aqueous electrolyte solution additive which may suppress electrodeposition on the surface of a negative electrode by scavenging metallic foreign matter included during the preparation of an electrode and transition metal ions dissolved from a positive electrode.

Another aspect of the present invention provides a non-aqueous electrolyte solution for a lithium secondary battery which includes the non-aqueous electrolyte solution additive.

Another aspect of the present invention provides a lithium secondary battery in which safety and life characteristics are improved by including the non-aqueous electrolyte solution for a lithium secondary battery.

Technical Solution

According to an aspect of the present invention,
there is provided a non-aqueous electrolyte solution additive which is a compound represented by Formula 1.

(Formula 1)

In Formula 1,

$R_1$ to $R_5$ are each independently $C-(R)_2$ or $C=O$, wherein R is hydrogen or an alkyl group having 1 to 3 carbon atoms.

The compound represented by Formula 1 may include at least one selected from the group consisting of compounds represented by Formulae 1a to 1d below.

(Formula 1a)

(Formula 1b)

(Formula 1c)

(Formula 1d)

According to another aspect of the present invention, there is provided a non-aqueous electrolyte solution for a lithium secondary battery including a lithium salt; an organic solvent; and the non-aqueous electrolyte solution additive of the present invention.

The non-aqueous electrolyte solution additive may be included in an amount of 0.05 wt % to 5 wt %, for example, 0.5 wt % to 3 wt % based on a total amount of the non-aqueous electrolyte solution.

According to another aspect of the present invention, there is provided a lithium secondary battery including a negative electrode, a positive electrode, a separator disposed between the negative electrode and the positive electrode, and a non-aqueous electrolyte solution, wherein the positive electrode includes at least one positive electrode active material selected from the group consisting of a lithium-nickel-manganese-cobalt-based oxide and a lithium-manganese-based oxide, and the non-aqueous electrolyte solution is the non-aqueous electrolyte solution for a lithium secondary battery of the present invention.

Specifically, the positive electrode active material may include a lithium-manganese-based oxide, and the lithium-manganese-based oxide may be $LiMn_2O_4$.

Advantageous Effects

According to an embodiment of the present invention, since a compound based on a cyclic sulfur structure is used as a non-aqueous electrolyte solution additive, electrodeposition on a surface of a negative electrode or reduction at the negative electrode may be suppressed by scavenging metallic foreign matter included during the preparation of an electrode and transition metal ions dissolved from a positive electrode. Therefore, it is possible to prevent a side reaction and an internal short-circuit by the metal ions, thereby improving low-voltage failure. Also, a lithium secondary battery having improved safety and life characteristics may be prepared by using a non-aqueous electrolyte solution including the non-aqueous electrolyte solution additive.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

As described above, transition metals constituting a positive electrode may be easily dissolved in an electrolyte solution due to HF generated in the electrolyte solution or structural variation of the positive electrode according to repeated charge and discharge, and the dissolved transition metal ions are redeposited on the positive electrode to be a cause of increasing resistance of the positive electrode. Also, since the transition metals moved to the negative electrode through the electrolyte solution are electrodeposited on the negative electrode to self-discharge the negative electrode and destruct a solid electrolyte interphase (SEI) that gives passivation ability to the negative electrode, interfacial resistance of the negative electrode is increased by promoting an additional electrolyte solution decomposition reaction.

Since this series of reactions reduces an amount of available lithium ions in a battery, it not only leads to the degradation of capacity of a battery, but an electrolyte solution decomposition reaction is also accompanied, and thus, resistance is also increased. Furthermore, in a case in which metal impurities are included in the electrode during the configuration of the electrode, metallic foreign matter is dissolved from the positive electrode and metal ions are electrodeposited on the surface of the negative electrode during initial charge. Since the electrodeposited metal ions grow as dendrites to cause an internal short-circuit of the battery, it causes low-voltage failure.

The present invention aims at providing a non-aqueous electrolyte solution additive which may have an effect of improving low voltage of the secondary battery by preventing the electrodeposition on the negative electrode or positive electrode by scavenging the dissolved metal ions, a cause of such degradation and failure behavior, in the battery.

Also, the present invention aims at providing a non-aqueous electrolyte solution, which may suppress degradation behavior of the secondary battery and simultaneously, may improve low-voltage failure by including the non-aqueous electrolyte solution additive, and a lithium secondary battery having improved safety and life characteristics.

Specifically, in an embodiment of the present invention, provided is a non-aqueous electrolyte solution additive which is a compound represented by Formula 1 below.

(Formula 1)

In Formula 1, $R_1$ to $R_5$ are each independently C—(R)$_2$ or C═O, wherein R is hydrogen or an alkyl group having 1 to 3 carbon atoms.

Specifically, the compound represented by Formula 1 may include at least one selected from the group consisting of compounds represented by Formulae 1a to 1d below.

(Formula 1a)

(Formula 1b)

(Formula 1c)

(Formula 1d)

Since the compound represented by Formula 1 has a structure based on a cyclic sulfur structure, the compound may scavenge transition metal ions dissolved from positive electrode material and impurities in the electrolyte solution. That is, the compound represented by Formula 1 is a multi-dentate macrocyclic ligand having cavities of similar size to transition metal ion species dissolved in the battery, wherein it may not suppress the dissolution of transition metal species, but may stabilize metal ions by binding strongly with the various transition metal ions at a ratio of 1:1 rather than binding with lithium ions in the electrolyte solution, and thus, the compound represented by Formula 1 may thermodynamically/dynamically suppress a reduction reaction. Therefore, the compound represented by Formula 1 may achieve an effect of suppressing a side reaction, which may occur in the negative electrode, by preventing the electrodeposition of the metal ions on the negative electrode.

Particularly, since the multi-dentate ligand has a considerably high bonding force with the metal ions in comparison to a ligand with low denticity, it is expected that the multi-dentate ligand may significantly improve the side reaction in the battery. That is, with respect to the metal ions bonded to the above compound, since a potential at which reduction thermodynamically occurs shifts in a negative direction and additional ligand desorption is required when the metal ions are reduced to metal, an effect is obtained in which the reaction is also dynamically slowed down. This means that the reduction reaction on the surface of the negative electrode becomes difficult. Thus, since the internal short-circuit and degradation of the battery may be suppressed and prevented, the low-voltage failure of the battery may be significantly improved, and, furthermore, safety and life characteristics may be dramatically improved.

In order to best achieve the effect, a size of the cavities of the macrocyclic ligand needs to be similar to a size of the transition metal ions used in a lithium-ion battery, and, specifically, the compound represented by Formula 1a is the most preferable among the above compounds.

However, in a case in which the number of carbon atoms and/or sulfur atoms increases so that a size of the ring becomes larger than that of the compound of the present invention like the compound of the following formula 2, since the cavities of the macrocyclic ligand are larger than the dissolved transition metal ion species, for example, metal ions of iron, nickel, manganese, cobalt, or copper, the macrocyclic ligand may not be strongly bonded to these metal ions, and thus, scavenging characteristics are relatively low. Therefore, the effect of improving low voltage or suppressing the degradation of the battery due to the dissolution of the metal ions may be reduced.

(Formula 2)

Also, in an embodiment of the present invention, provided is a non-aqueous electrolyte solution for a lithium secondary battery including:

a lithium salt;
an organic solvent; and
the non-aqueous electrolyte solution additive of the present invention.

In this case, the compound represented by Formula 1 may be included in an amount of 0.05 wt % to 5 wt %, particularly 0.5 wt % to 3 wt %, and more particularly 0.1 wt % to 1 wt % based on a total amount of the non-aqueous electrolyte solution.

In a case in which the compound represented by Formula 1 is included within the above range, a secondary battery having more improved overall performance may be prepared. For example, if the amount of the additive is more than 0.05 wt %, an amount of the metal ions, which may be scavenged, is increased, and, if the amount of the additive is less than 5 wt %, a side reaction due to the excessive amount of the additive used, for example, an increase in resistance of the electrolyte solution may be suppressed.

Thus, the metal ions dissolved from the positive electrode are precipitated on the negative electrode when a conventional non-aqueous electrolyte solution is used, but, in a case in which the non-aqueous electrolyte solution including the compound based on the cyclic sulfur structure as an additive is used as in the present invention, since the metal ions dissolved from the positive electrode and the compound of Formula 1 are bonded to scavenge the metal ions, the precipitation of the metal ions on the negative electrode may be reduced. Accordingly, charge and discharge efficiency of the lithium secondary battery may be improved and good cycle characteristics may be obtained. In addition, the lithium secondary battery including the non-aqueous electrolyte solution of the present invention may improve capacity characteristics in both normal and high voltage ranges. Furthermore, since the internal short-circuit due to the metal precipitation on the negative electrode may be suppressed, the low-voltage failure may be improved.

The expression "normal voltage" used in the present specification denotes a case in which a charge voltage of the lithium secondary battery is in a range of 3.0 V to less than 4.3 V, and, the expression "high voltage" denotes a case in which the charge voltage is in a range of 4.3 V to 5.0 V.

In the non-aqueous electrolyte solution of the present invention, the lithium salt, which is included as an electrolyte, may be used without limitation so long as it is typically used in an electrolyte solution for a lithium secondary battery, and, for example, the lithium salt, which includes $Li^+$ as a cation and includes any one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion, may be used.

In the non-aqueous electrolyte solution of the present invention, the organic solvent is not limited as long as it may minimize decomposition due to an oxidation reaction during charge and discharge of the battery and may exhibit desired characteristics with the additive. For example, an ether-based solvent, an ester-based solvent, or an amide-based solvent may be used alone or in mixture of two or more thereof.

As the ether-based solvent among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a cyclic carbonate compound, a linear carbonate compound, a linear ester compound, and a cyclic ester compound.

Among these compounds, specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Also, specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

Specific examples of the linear ester compound may be any one selected from the group consisting of methyl acetate, ethyl acetate, propyl acetate, methyl propionate, ethyl propionate, propyl propionate, and butyl propionate, or a mixture of two or more thereof, but the present invention is not limited thereto.

Specific examples of the cyclic ester compound may be any one selected from the group consisting of γ-butyrolactone, γ-valerolactone, γ-caprolactone, σ-valerolactone, and ε-caprolactone, or a mixture of two or more thereof, but the present invention is not limited thereto.

Among the ester-based solvents, since the cyclic carbonate-based compound well dissociates the lithium salt in the electrolyte due to high permittivity as a highly viscous organic solvent, the cyclic carbonate-based compound may be preferably used. Since an electrolyte solution having high electrical conductivity may be prepared when the above cyclic carbonate-based compound is mixed with the low viscosity, low permittivity linear carbonate-based compound, such as dimethyl carbonate and diethyl carbonate, and the linear ester-based compound in an appropriate ratio, the cyclic carbonate-based compound may be more preferably used.

The non-aqueous electrolyte solution of the present invention may further include an additive for forming an SEI, if necessary. As the additive for forming an SEI which may be used in the present invention, a silicon-based compound including a vinyl group, vinylene carbonate, vinyl ethylene carbonate, fluoroethylene carbonate, cyclic sulfite, saturated sultone, unsaturated sultone, and a non-cyclic sulfone may be used alone or in a mixture of two or more thereof.

In this case, the cyclic sulfite may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, the saturated sultone may include 1,3-propane sultone and 1,4-butane sultone, the unsaturated sultone may include ethene sultone, 1,3-propene sultone, 1,4-butene sultone, and 1-methyl-1,3-propene sultone, and the non-cyclic sulfone may include divinyl sulfone, dimethyl sulfone, diethyl sulfone, methyl ethyl sulfone, and methyl vinyl sulfone.

Also, in an embodiment of the present invention, provided is a secondary battery including a negative electrode, a positive electrode, a separator disposed between the negative electrode and the positive electrode, and a non-aqueous electrolyte solution, wherein the positive electrode includes a positive electrode active material selected from the group consisting of a lithium-nickel-manganese-cobalt-based oxide and a lithium-manganese-based oxide, and the non-aqueous electrolyte solution is the non-aqueous electrolyte solution for a secondary battery of the present invention.

The lithium secondary battery of the present invention may be prepared by injecting the non-aqueous electrolyte solution of the present invention into an electrode assembly composed of the positive electrode, the negative electrode, and the separator disposed between the positive electrode and the negative electrode. In this case, any positive electrode, negative electrode, and separator, which have typically been used in the preparation of a lithium secondary battery, may be used as the positive electrode, negative electrode, and separator which constitute the electrode assembly.

Specifically, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has high conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include a lithium transition metal oxide including lithium and at least one metal selected from cobalt, manganese, nickel, or aluminum, and, specifically, the positive electrode active material may include a lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or lithium-manganese-based oxide having high capacity characteristics and stability of the battery, and, for example, may include a lithium-manganese-based oxide.

The lithium-nickel-manganese-cobalt-based oxide may include at least one of $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, and $Li(Ni_{0.8}Mn_{0.1}Co_{0.1})O_2$), and the lithium-manganese-based oxide may be $LiMn_2O_4$.

That is, with respect to the compound of Formula 1 of the present invention, since it has a sulfur (S) atom-based macrocyclic structure with a cavity size that is compatible with nickel (Ni), cobalt (Co), manganese (Mn), copper (Cu), or iron (Fe), which are transition metals used in the positive electrode material of the lithium-ion battery, it may rapidly scavenge the transition metal ions in the electrolyte solution, which are generated by the dissolution from the positive electrode or the dissolution due to oxidation of metallic impurities of the positive electrode, in comparison to a compound having a macrocyclic ring in which the number of sulfur atoms is 5 or more, a compound having a small ring in which the number of sulfur atoms is 3 or less, or a sultone-based compound. Thus, since the side reaction, in which the transition metal ions are electrodeposited on the negative electrode, which is a major cause of degradation of the battery, may be suppressed, the degradation of the battery may be effectively suppressed. Therefore, in a case in which the lithium-manganese-based oxide, in which the dissolution of excessive amount of transition metal occurs, is used in the positive electrode active material, since the compound of Formula 1 of the present invention may suppress degradation behavior due to the dissolution of the transition metal, better battery performance may be achieved.

In addition to the lithium-nickel-manganese-cobalt-based oxide or lithium-manganese-based oxide, the positive electrode active material of the present invention may further include at least one lithium transition metal oxide selected from the group consisting of lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-y}Mn_yO_2$ (where $0<Y<1$), $LiMn_{2-z}Ni_zO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), $Li(Ni_{p1}Co_{q1}Mn_{r2})O_4$ (where $0<p1<2$, $0<q1<2$, $0<r2<2$, and $p1+q1+r2=2$), etc.), and lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$)).

The positive electrode active material may be included in an amount of 80 wt % to 99 wt % based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

The conductive agent is commonly added in an amount of 1 wt % to 30 wt % based on the total weight of the solid content in the positive electrode slurry.

Any conductive agent may be used as the conductive agent without particular limitation so long as it has conductivity without causing adverse chemical changes in the battery, and, for example, a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 50 wt % to 95 wt %, for example, 70 wt % to 90 wt %.

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material. The negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metals or alloys of lithium and these metals, a metal composite oxide, a material which may be doped and undoped with lithium, and a transition metal oxide.

As the carbon material capable of reversibly intercalating/deintercalating lithium ions, any carbon material may be used without particular limitation so long as it is a carbon-based negative electrode active material generally used in a lithium ion secondary battery, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metals or alloys of lithium and these metals, metals selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn) or alloys of lithium and these metals may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_z$ (Me: manganese (Mn), iron (Fe), Pb, or Ge; Me': Al, boron (B), phosphorus (P), Si, Groups I, II and III elements of the periodic table, or halogen; $0<x\leq1$; $1\leq y\leq3$; $1\leq z\leq8$) may be used as the metal composite oxide.

The material, which may be doped and undoped with lithium, may include Si, $SiO_x$ ($0<x\leq2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), Rf, V, niobium (Nb), Ta, dubidium (Db), Cr, Mo, tungsten (W), seaborgium (Sg), Tc (technetium), rhenium (Re), Bh (bohrium), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), Po (polonium), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode active material slurry.

The binder is a component that assists in the binding between the conductive agent, the active material, and the current collector, wherein the binder is commonly added in an amount of 1 wt % to 30 wt % based on the total weight of the solid content in the negative electrode active material slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode active material slurry. Any conductive agent may be used as the conductive agent without particular limitation so long as it has conductivity without causing adverse chemical changes in the battery, and, for example, a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as N-methyl-2-pyrrolidone (NMP) and alcohol, and may be used in an amount such that desirable viscosity is obtained when the negative electrode active material as well as selectively the binder and the conductive agent are included. For example, the solvent may be included in an amount such that a concentration of the solid content in the slurry including the negative electrode active material as well as selectively the binder and the conductive agent is in a range of 50 wt % to 95 wt %, for example, 70 wt % to 90 wt %.

Also, the separator plays a role in blocking an internal short-circuit between both electrodes and impregnating the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 µm to 50 µm and a porosity of 5% to 95%. Also, the porous separator may generally have a thickness of 5 µm to 300 µm.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

A non-aqueous electrolyte solution of the present invention was prepared by adding 0.025 g of the compound of Formula 1a to 4.975 g of an organic solvent (ethylene carbonate:ethyl methyl carbonate=30:70 vol %) in which 1.0M $LiPF_6$ was dissolved.

(Positive Electrode Preparation)

A 20 µm thick positive electrode collector (Al foil) was coated with a mixture, in which a ternary positive electrode active material ($Li(Ni_{0.8}Mn_{0.1}Co_{0.1})O_2$) containing nickel, cobalt, and manganese, as a positive electrode active material, carbon black as a conductive agent, and polyvinylidene fluoride (PVDF), as a binder, were mixed in a ratio of 97.5:1:1.5 (wt %), dried, and roll-pressed to prepare a positive electrode. A surface of the electrode thus prepared was coated with about 0.5 $mg/cm^2$ to about 0.6 $mg/cm^2$ of iron particles to prepare a positive electrode for a low-voltage failure simulation test.

(Secondary Battery Preparation)

The positive electrode including impurities, which was prepared by the above-described method, a negative electrode using lithium (Li) metal, and a porous polyethylene separator were used to prepare a coin half-cell.

Example 2

A non-aqueous electrolyte solution and a coin half-cell including the same were respectively prepared in the same manner as in Example 1 except that 0.05 g of the compound of Formula 1a was added to 4.95 g of the organic solvent during the preparation of the non-aqueous electrolyte solution.

Example 3

A non-aqueous electrolyte solution and a coin half-cell including the same were respectively prepared in the same manner as in Example 1 except that 0.015 g of the compound of Formula 1a was added to 4.985 g of the organic solvent during the preparation of the non-aqueous electrolyte solution.

Comparative Example 1

A non-aqueous electrolyte solution and a coin half-cell including the same were prepared in the same manner as in Example 1 except that an additive was not included during the preparation of the non-aqueous electrolyte solution (see Table 1 below).

Comparative Example 2

A non-aqueous electrolyte solution and a coin half-cell including the same were prepared in the same manner as in Example 2 except that a compound of the following Formula 3 was included as an additive during the preparation of the non-aqueous electrolyte solution (see Table 1 below).

[Formula 3]

Comparative Example 3

A non-aqueous electrolyte solution and a coin half-cell including the same were prepared in the same manner as in Example 2 except that a compound of the following Formula 4 was included as an additive during the preparation of the non-aqueous electrolyte solution (see Table 1 below).

[Formula 4]

TABLE 1

| Examples | Organic solvent | | Additive | | |
|---|---|---|---|---|---|
| | Lithium salt | Composition | Amount added (g) | Formula | Amount added (g) | (wt %) |
| Example 1 | | EC:EMC = 30:70 (vol %) | 4.975 | 1a | 0.025 | 0.5 |
| Example 2 | | | 4.95 | 1a | 0.05 | 1 |
| Example 3 | 1.0M LiPF$_6$ | | 4.985 | 1a | 0.015 | 0.3 |
| Comparative Example 1 | | | 5 | — | — | — |
| Comparative Example 2 | | | 4.95 | 3 | 0.05 | 1 |
| Comparative Example 3 | | | 4.95 | 4 | 0.05 | 1 |

EXPERIMENTAL EXAMPLES

Experimental Example 1

After the coin half-cells prepared in Example 1 and Comparative Example 1 were respectively prepared in a dry room and were maintained in a 25° C. thermostat for 24 hours, a change in voltage of each coin half-cell with time was measured while performing constant current-constant voltage (CC-CV) charge and discharge at 0.1C within a voltage range of 3.0 V to 4.25 V (vs. Li/Li$^+$). In this case, a CV current termination condition was set at 0.05C.

Figure 1:
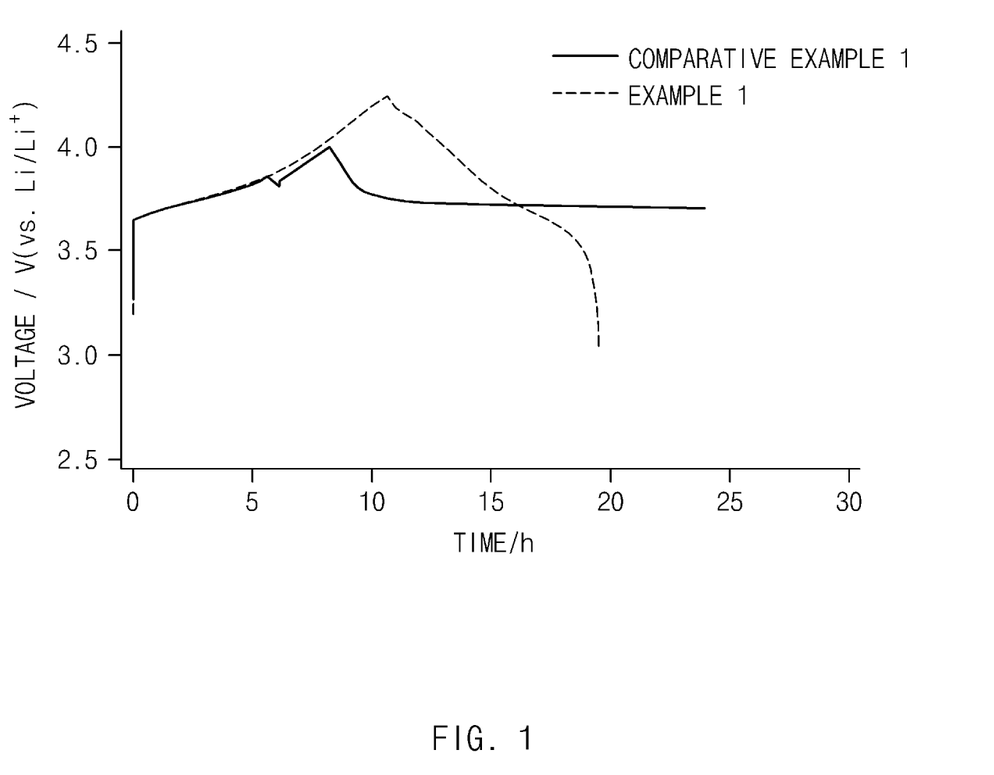
FIG. 1 is a graph illustrating changes in voltages of coin half-cells with time in Experimental Example 1 of the present invention.

As a result, as illustrated in FIG. 1, with respect to the coin half-cell of Example 1, it was normally charged and discharged, wherein a closed circuit voltage (CCV) of 4.25 V was reached during the charge and the voltage was discharged when the discharge began, but, with respect to the coin half-cell of Comparative Example 1, since the voltage did not reach 4.25 V during initial charge and an internal short-circuit occurred, it may be understood that a graph, in which the voltage dropped even when an oxidation current was applied to the positive electrode, was appeared.

That is, if the voltage of the coin half-cell increased above a potential at which iron powder may be dissolved because an oxidation reaction occurred at the positive electrode during the constant current process, iron (Fe) was dissolved from the positive electrode, and the iron (Fe) thus dissolved formed dendrites, while being electrodeposited on the surface of the Li metal as the negative electrode, to cause the internal short-circuit. As a result, with respect to the coin half-cell of Comparative Example 1, the graph, in which a charge end voltage was not reached and the potential dropped as illustrated in FIG. 1, was appeared.

In contrast, since the coin half-cell of Example 1 included the macrocyclic ligand including S as an additive in the non-aqueous electrolyte solution, the additive prevents the formation of dendrites due to the reduction of iron on the surface of the negative electrode by scavenging iron ions dissolved from the positive electrode, and thus, an internal short-circuit hardly occurred. Therefore, it may be understood that the graph confirmed that normal charge and discharge proceeded as illustrated in FIG. 1.

Experimental Example 2

While 6 of each of the coin half-cells prepared in Examples 1 to 3 and the coin half-cells prepared in Comparative Examples 1 to 3 were charged and discharged under the same condition as in Experimental Example 1, it was confirmed whether or not an internal short-circuit of each coin half-cell occurred. From the results thus obtained, a degree of occurrence of the internal short-circuit (failure rate) of each of the coin half cells of Examples 1 to 3 and Comparative Examples 1 to 3 was measured, and the results thereof are then presented in Table 2 below. In this case, if an internal short-circuit occurrence rate is high in Table 2, it denotes that a low-voltage occurrence rate (failure rate) of the secondary battery is high.

TABLE 2

| | The number of coin half-cells in which internal short-circuit occurred (occurrence/preparation) | Internal short-circuit occurrence (failure rate) (%) |
|---|---|---|
| Example 1 | 0/6 | 0 |
| Example 2 | 0/6 | 0 |
| Example 3 | 0/6 | 0 |
| Comparative Example 1 | 4/6 | 66 |
| Comparative Example 2 | 2/6 | 33 |
| Comparative Example 3 | 6/9 | 66.7 |

As illustrated in Table 2, with respect to Comparative Example 1 in which the non-aqueous electrolyte solution without an additive was used, it may be understood that an internal short-circuit occurrence rate was about 66% due to the decomposition product of the lithium salt and the dissolution of the metal included in the positive electrode during charge. As a result, if a positive electrode reduction reaction occurs, a sudden voltage drop occurs, and it may be predicted that the failure rate (low-voltage occurrence rate) is increased.

In contrast, with respect to the coin half-cells of Examples 1 to 3, since the macrocyclic ligand including a sulfur atom was included as an additive in the non-aqueous electrolyte solution, the additive prevents the formation of dendrites on the surface of the negative electrode by scavenging metal impurities dissolved in the electrolyte solution, and thus, it may be confirmed that an internal short-circuit hardly occurred in comparison to Comparative Example 1.

With respect to the coin half-cell of Comparative Example 2 in which the non-aqueous solution including the compound of Formula 3, a bidentate compound with low denticity containing a nitrogen atom, as an additive was used, a low-voltage occurrence rate (failure rate) was about 33%, wherein it may be confirmed that performance was relatively degraded in comparison to those of Examples 1 to 3.

Also, with respect to the coin half-cell of Comparative Example 3 in which the non-aqueous solution including the sultone-based compound of Formula 4 as an additive was used, a low-voltage occurrence rate (failure rate) was about 66.7%, wherein it may be confirmed that performance was significantly degraded in comparison to those of Examples 1 to 3.

Experimental Example 3. Metal (Mn) Dissolution Suppression Evaluation Test

A lithium-manganese-based active material (LiMn$_2$O$_4$) as a positive electrode active material, carbon black as a conductive agent, and polyvinylidene fluoride (PVDF), as a binder, were mixed in a ratio of 90:7.5:2.5 (wt %) to prepare a positive electrode slurry, and a 20 μm thick positive electrode collector (Al foil) was then coated with the slurry, dried, and roll-pressed to prepare a positive electrode.

Subsequently, the positive electrode was put in 5 mL of the non-aqueous electrolyte solution prepared in Example 2 and 5 mL of the non-aqueous electrolyte solution prepared in Comparative Example 1 and stored at a state of charge (SOC) of 0% for 2 weeks at 60° C., and a concentration of metal (Mn) dissolved in the electrolyte solution was then measured using an inductively coupled plasma optical emission spectrophotometer (ICP-OES). An amount of the metal measured using ICP analysis is presented in FIG. 2 below.

Figure 2:
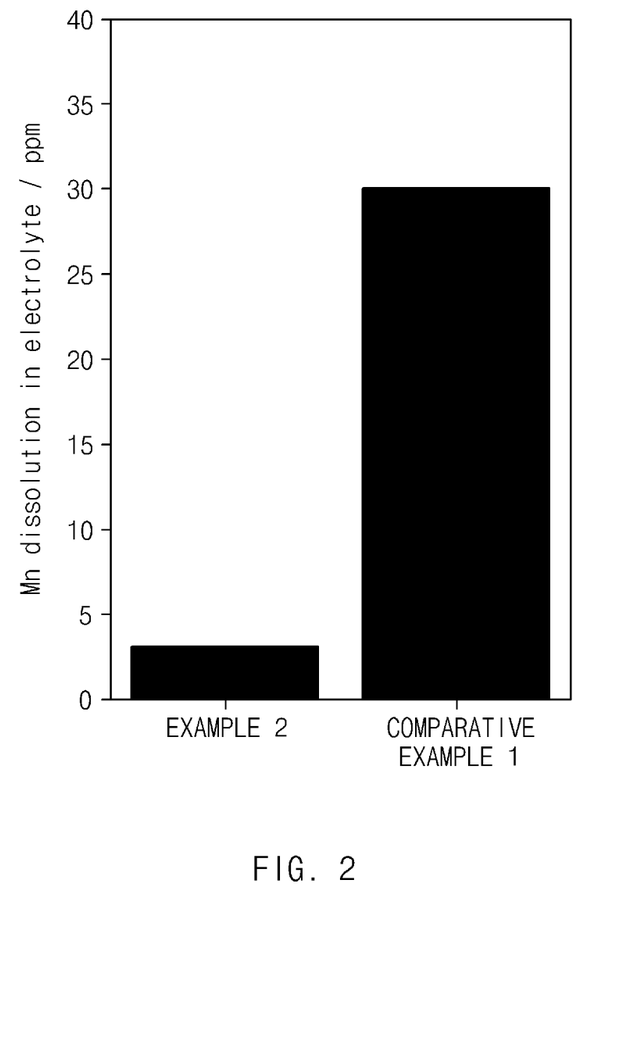
FIG. 2 is a graph illustrating metal dissolution suppression effects of non-aqueous electrolyte solutions in Experimental Example 3 of the present invention.

Referring to FIG. 2, in a case in which the non-aqueous electrolyte solution of Example 2 of the present invention was used, since the compound containing a macrocyclic ligand based on a sulfur atom, which was included as the additive, scavenges the metal ions dissolved in the electrolyte solution by forming a complex with Mn ions, an effect of suppressing the dissolution of the metal from the positive electrode including the lithium-manganese-based oxide was significantly improved in comparison to that of the non-aqueous electrolyte solution of Comparative Example 1 without an additive, and thus, it may be confirmed that less Mn ions were detected.

The invention claimed is:

1. A non-aqueous electrolyte solution additive which is a compound represented by Formula 1:

(Formula 1)

wherein, in Formula 1,
R$_1$ to R$_5$ are each independently C—(R)$_2$ or C═O, wherein R in each R$_1$ to R$_5$ when being C—(R)$_2$ is same or different, and is selected from hydrogen or an alkyl group having 1 to 3 carbon atoms, and at least one of R$_1$ to R$_5$ is C—(R)$_2$ or C═O, wherein R is an alkyl group having 1 to 3 carbon atoms.

2. The non-aqueous electrolyte solution additive of claim 1, wherein the compound represented by Formula 1 comprises at least one selected from the group consisting of compounds represented by Formulae 1b to 1d:

(Formula 1b)

(Formula 1c)

(Formula 1d)

3. A non-aqueous electrolyte solution for a lithium secondary battery, the non-aqueous electrolyte solution comprising:
a lithium salt;
an organic solvent; and
a non-aqueous electrolyte solution additive,
wherein the non-aqueous electrolyte solution additive is the non-aqueous electrolyte solution additive of claim 1.

4. The non-aqueous electrolyte solution for a lithium secondary battery of claim 3, wherein the non-aqueous electrolyte solution additive is included in an amount of 0.05 wt % to 5 wt % based on a total amount of the non-aqueous electrolyte solution.

5. The non-aqueous electrolyte solution for a lithium secondary battery of claim 4, wherein the non-aqueous electrolyte solution additive is included in an amount of 0.5 wt % to 3 wt % based on the total amount of the non-aqueous electrolyte solution.

6. A lithium secondary battery comprising a negative electrode, a positive electrode, a separator disposed between the negative electrode and the positive electrode, and a non-aqueous electrolyte solution,
wherein the positive electrode comprises at least one positive electrode active material selected from the group consisting of a lithium-nickel-manganese-cobalt-based oxide and a lithium-manganese-based oxide, and
the non-aqueous electrolyte solution is the non-aqueous electrolyte solution for a lithium secondary battery of claim 3.

7. The lithium secondary battery of claim 6, wherein the positive electrode active material comprises a lithium-manganese-based oxide.

8. The lithium secondary battery of claim 7, wherein the lithium-manganese-based oxide is $LiMn_2O_4$.

9. The non-aqueous electrolyte solution for a lithium secondary battery of claim 3, wherein the lithium salt comprises $Li^+$ as a cation, and any one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion.

10. The non-aqueous electrolyte solution for a lithium secondary battery of claim 3, wherein the organic solvent comprises at least one selected from an ether-based solvent, an ester-based solvent, or an amide-based solvent.

11. The non-aqueous electrolyte solution for a lithium secondary battery of claim 3, wherein the organic solvent comprises at least one selected from a cyclic carbonate compound, a linear carbonate compound, a linear ester compound, or a cyclic ester compound.

12. The non-aqueous electrolyte solution for a lithium secondary battery of claim 11, wherein the linear carbonate compound comprises at least one selected from the group consisting of dimethyl carbonate (DMC), diethyl carbonate (DEC), dipropyl carbonate, ethylmethyl carbonate (EMC), methylpropyl carbonate, and ethylpropyl carbonate.

13. The non-aqueous electrolyte solution for a lithium secondary battery of claim 11, wherein the cyclic carbonate compound comprises at least one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate.

14. The non-aqueous electrolyte solution for a lithium secondary battery of claim 3, further comprising an additive selected from a silicon-based compound including a vinyl group, vinylene carbonate, vinyl ethylene carbonate, fluoroethylene carbonate, cyclic sulfite, saturated sultone, unsaturated sultone, a non-cyclic sulfone, or a combination thereof.

15. The lithium secondary battery of claim 6, wherein the positive electrode active material further comprises at least one lithium transition metal oxide selected from the group consisting of lithium-cobalt-based oxide, lithium-nickel-based oxide, lithium-nickel-manganese-based oxide, lithium-nickel-cobalt-based oxide, lithium-manganese-cobalt-based oxide, and lithium-nickel-cobalt-transition metal oxide.

* * * * *